(12) United States Patent
Dongar et al.

(10) Patent No.: US 7,407,504 B2
(45) Date of Patent: Aug. 5, 2008

(54) DEVICE FOR IMMOBILISHING AN OSTEOSYNTHESIS PIN IN A BONE PART

(76) Inventors: Christian Dongar, 20ter, rue des Docteurs Daréne, F-95270 Viarmes (FR); Alexandre Worcel, 110, allée des Catalpas, Parc de Mongarny, F-95680 Montlignon (FR)

( * ) Notice: Subject to any disclaimer, the term of this patent is extended or adjusted under 35 U.S.C. 154(b) by 0 days.

(21) Appl. No.: 10/541,231

(22) PCT Filed: Jan. 15, 2004

(86) PCT No.: PCT/FR2004/000070

§ 371 (c)(1), (2), (4) Date: Jan. 19, 2006

(87) PCT Pub. No.: WO2004/069067

PCT Pub. Date: Aug. 19, 2004

(65) Prior Publication Data
US 2006/0155275 A1 Jul. 13, 2006

(30) Foreign Application Priority Data
Jan. 15, 2003 (FR) .................................. 03 00393

(51) Int. Cl.
*A61F 5/04* (2006.01)
(52) U.S. Cl. ........................................................ 606/59
(58) Field of Classification Search .................. 606/54, 606/57, 59, 60, 61, 72, 73
See application file for complete search history.

(56) References Cited

U.S. PATENT DOCUMENTS

| 4,388,921 | A | * | 6/1983 | Sutter et al. | 606/71 |
| 4,621,961 | A | * | 11/1986 | Gulistan | 411/352 |
| 5,141,357 | A | * | 8/1992 | Sherman et al. | 403/408.1 |
| 5,209,620 | A | * | 5/1993 | Zare-Ardestani | 411/104 |
| 5,304,179 | A | | 4/1994 | Wagner | |
| 5,393,161 | A | | 2/1995 | Mata et al. | |
| 5,735,853 | A | * | 4/1998 | Olerud | 606/71 |
| 5,902,303 | A | * | 5/1999 | Eckhof et al. | 606/60 |
| 5,976,141 | A | * | 11/1999 | Haag et al. | 606/72 |
| 6,280,445 | B1 | | 8/2001 | Morrison et al. | |
| 2004/0254579 | A1 | * | 12/2004 | Buhren et al. | 606/71 |
| 2006/0195104 | A1 | * | 8/2006 | Schlafli et al. | 606/72 |

FOREIGN PATENT DOCUMENTS

EP  517939 A1 * 12/1992

* cited by examiner

*Primary Examiner*—Eduardo C. Robert
*Assistant Examiner*—Nicholas Woodall
(74) *Attorney, Agent, or Firm*—Young & Thompson

(57) ABSTRACT

A device which is used to immobilize a threaded support pin (21) in relation to a fixed element (1, 34), the pin being screwed into a bone part (3, 3a, 3b) along an axis. A locking sleeve (13) can be solidly screwed to the fixed element (1, 34, 7) and is provided with an axial bore (19) in order to receive the pin (21). The axis (zz') of the sleeve screw thread is angularly and/or laterally offset in relation to the axis (yy') of the pin (21) when the latter is in place on the bone part (3, 3a, 3b), and/or the axis of the bore (19) of the locking sleeve (13) is angularly and/or laterally offset in relation to the screw threaded axis (6).

1 Claim, 5 Drawing Sheets

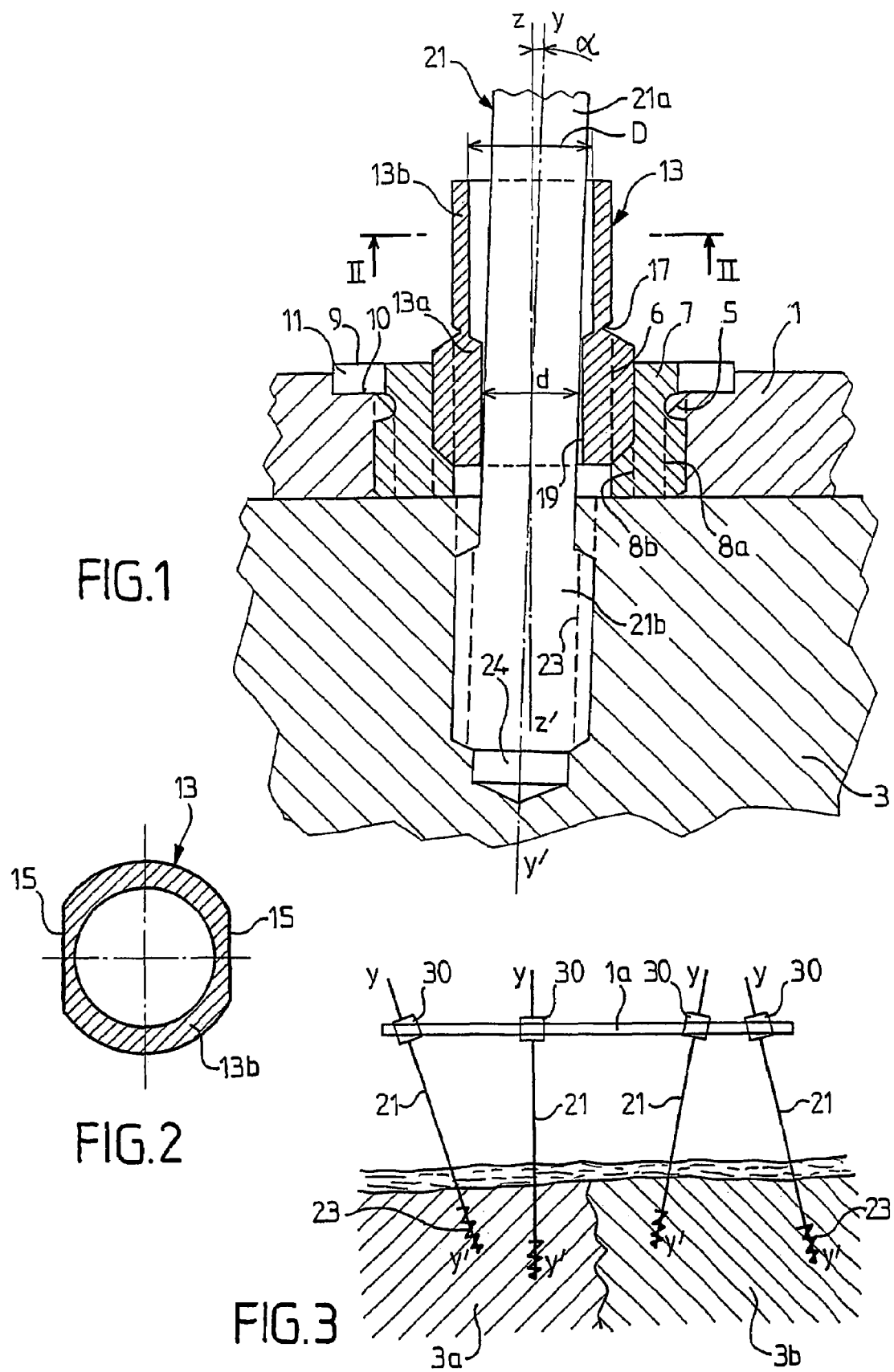

DEVICE FOR IMMOBILISHING AN OSTEOSYNTHESIS PIN IN A BONE PART

The present invention relates to a device for immobilising on a fixed element, particularly constituted by an osteosynthesis plate, a threaded support pin screwed in a bone part.

Various devices of the prior state of the art, which are able to ensure such a fixation, are known. For example, it has been proposed to use screws of conventional type of which the head is countersunk at 45°, this making it possible to embed it inside a recess of the same shape provided in the plate, so that no aggressive or blunt part exists outside of the latter. In a variant embodiment, it has been proposed to obturate the upper part of the recess containing the head of the screw with the aid of a nut in the form of a pellet which is screwed in a corresponding threading provided at the entrance of said recess. Although such a device makes it possible to avoid any projection or surface discontinuity with that of the plate, it nonetheless presents the drawback, in the case of the threading of this nut being damaged, of preventing any dismantling of the locking screw.

Furthermore, such a device also presents the drawback, when the axis of the threaded hole made in the bone part does not strictly merge with that of said truncated cavity, of creating stresses at the level of the bone part, which stresses are likely in the course of time to affect the integrity of the bone part and consequently to be detrimental to the correct fixation of the plate.

In order to avoid such a drawback, it has been proposed to provide the plate with an intermediate element constituting a sort of spherical ball-joint inside which is provided the truncated housing intended to receive the head of the locking screw. Under these conditions, it will be understood that the spherical ball-joint makes it possible to compensate the defects of alignment of said cavity with the axis of the hole receiving the screw. Although such a device thus makes it possible to avoid the mechanical stresses previously mentioned, occurring at the level of the plate and the bone part, it nonetheless presents the drawback, insofar as it creates a new degree of freedom between the plate and the screw, of avoiding "the block structure effect" which occurs when a plurality of locking screws are fast with the same plate. In effect, in such a case, it has been observed that, even if the locking screws are hardly tightened on the bone part, the fact that these screws are fast with the plate and penetrate in the bone part along different axes, constitutes a sort of hyperstatic system ensuring a connection of the plate. Now, such an arrangement is particularly interesting insofar as, most often, the bone parts in which the screws are positioned relate to pathologies affecting their mechanical quality, so that not only the positioning of these screws does not reinforce this mechanical quality but, on the contrary, it tends rathermore to reduce it and even totally eliminate it when too great an effort of tightening is exerted.

Furthermore, it will be noted that, in the case of open fractures, such support devices are totally inoperative, since they must in that case be moved away from the patient's skin surface, so that it is not possible in that case to employ osteosynthesis plates.

Finally, the different support devices of the prior state of the art which employ screws present the servitude of obliging the practitioner to have available a complete assortment of them both concerning their length and their diameter. This is why hospital operating centres are obliged to have available, monitor and maintain available a considerable stock of screws, this representing considerable cost, on the one hand concerning the raw material itself and, on the other hand concerning logistics.

The present invention has for an object to propose an immobilising device allowing a practitioner, on the one hand, to adjust the length of the screws used as a function of the application, this avoiding the problem of storage of the screws, and, on the other hand, making it possible to ensure immobilisation of the bone parts in the case of open fractures.

The present invention thus has for its object a device for immobilising with respect to a fixed element a threaded support pin screwed in a bone part along an axis, characterized in that it comprises a locking sleeve which is connectable by screwing of the fixed element, which is provided with an axial bore which receives the pin, the axis of the threading of this sleeve is angularly and/or laterally offset in relation to the axis of the pin when the latter is in place on the bone part, and/or the axis of the bore of the locking sleeve is angularly and/or laterally offset in relation to the axis of the threading In order to promote dismantling of the device, an intermediate piece adapted to be fixed on the fixed element may be disposed between the latter and the locking sleeve.

In a form of embodiment of the invention, the intermediate piece may be constituted by a sleeve provided with an external threading by which it is screwed in the fixed element, the axis of the external threading of this intermediate sleeve merging with the axis of the pin when the latter is in place on the bone part. As for the fixed element, it may be constituted by a plate which will be applied against the bone part and will be intended to be connected thereto.

According to the invention, the threaded part of the locking sleeve may extend outwardly by a gripping element for driving the latter in rotation, and a zone of lesser resistance with controlled shear rupture level will be provided between said threaded part and the gripping element. The intermediate sleeve may comprise in its upper part a circular boss forming stop, intended to come into abutment on the plate, particularly in a recess therein. This circular boss may comprise a series of orifices intended to ensure gripping and drive in rotation thereof in order to block/unblock the intermediate sleeve on the plate.

In another form of embodiment of the invention, the fixed element will be constituted by a support receiving intermediate pieces which will be mounted mobile, on the one hand, along the profile of the support and, on the other hand, in rotation, fixing means ensuring the immobilisation of the intermediate pieces with respect to the fixed element. This fixed element may in particular be constituted by a rail of which the internal profile will be of hemispherical shape and whose base will be pierced with a longitudinal slot adapted to be traversed by the threaded pins. The intermediate pieces will be constituted by spheres adapted to be positioned at any point of the rail, and the device will comprise an upper cover of hemispherical internal profile of which the apex will be pierced with a longitudinal slot adapted to be traversed by the threaded pins, and tightening means adapted to apply the spherical intermediate pieces against the rail in order to immobilise them both in translation and in rotation with respect thereto.

A form of embodiment of the present invention will be described hereinafter by way of non-limiting example, with reference to the accompanying drawings, in which:

FIG. 1 is a view in longitudinal section of an immobilising device according to the invention which is placed on a bone part.

FIG. 2 is a view in transverse section of the device shown in FIG. 1, along line II-II thereof.

FIG. 3 is a schematic view of a second example of application of the immobilising device according to the invention.

Figure 7:
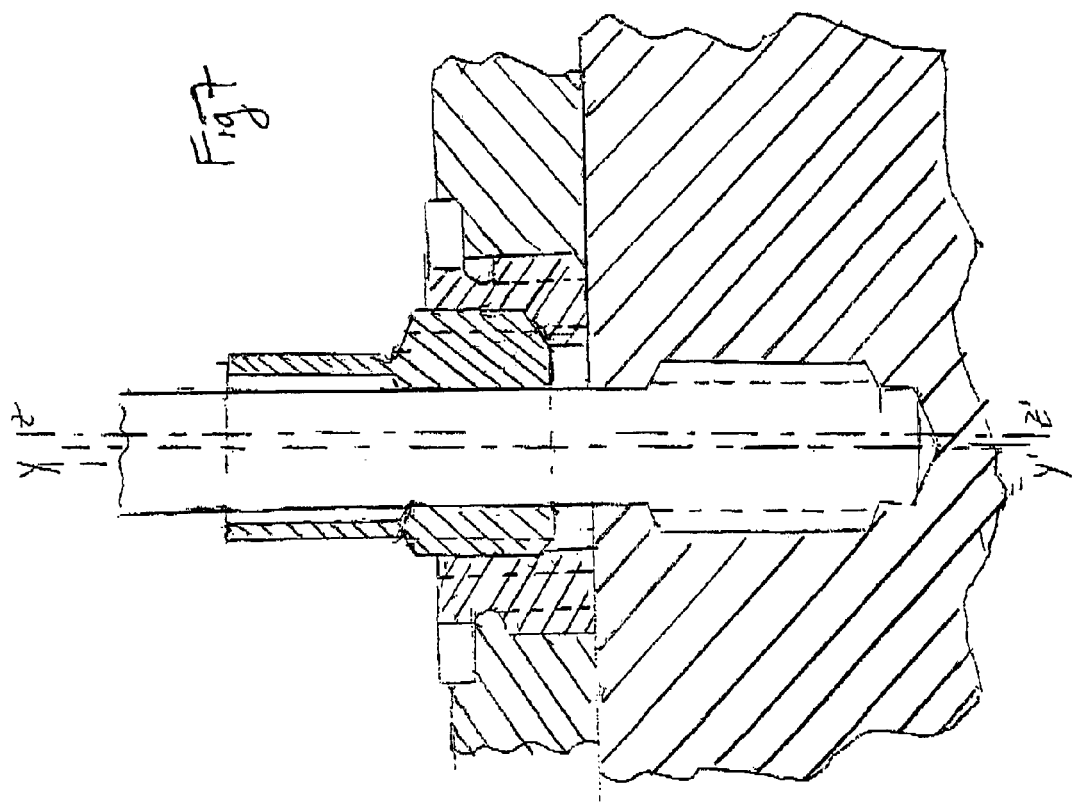
FIG. 7 is a view similar to FIG. 1 but wherein the axis of the external threading of the locking sleeve is laterally offset in relation to the axis of the pin.
Figure 8:
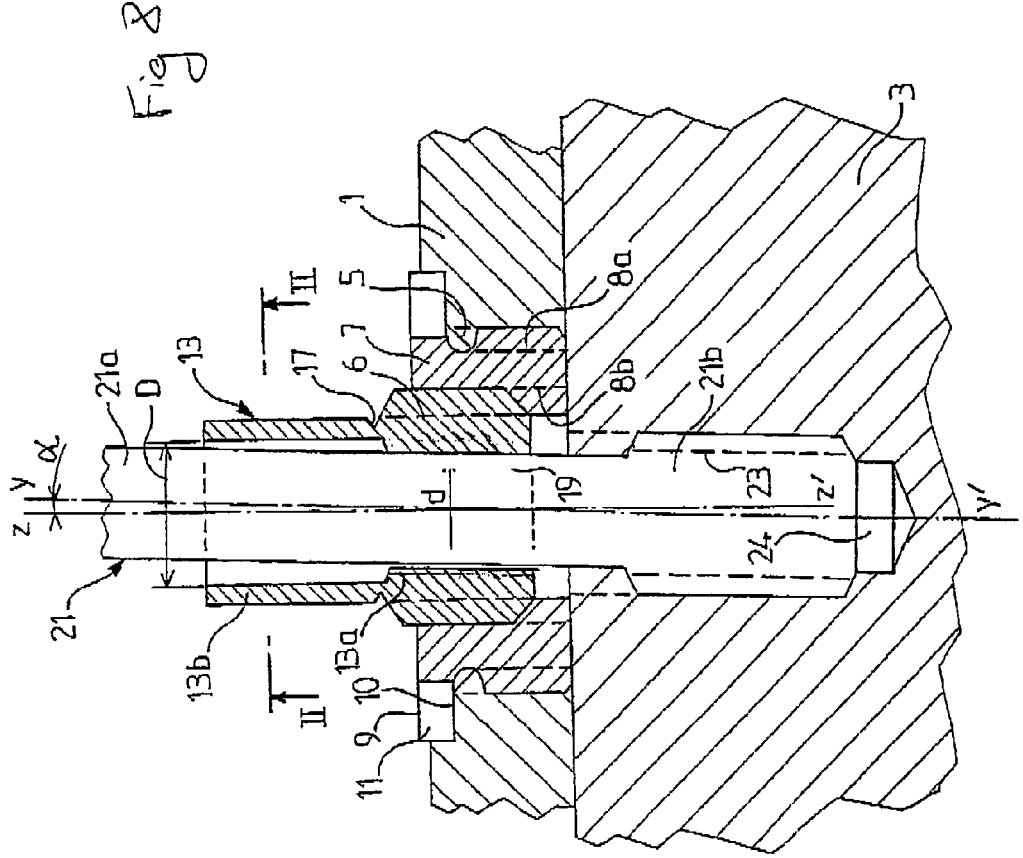
FIG. 8 is a view similar to FIGS. 1 and 7, but wherein the axis of the bore of the locking sleeve is angularly offset in relation to the axis of the external threading of the locking sleeve.
Figure 9:
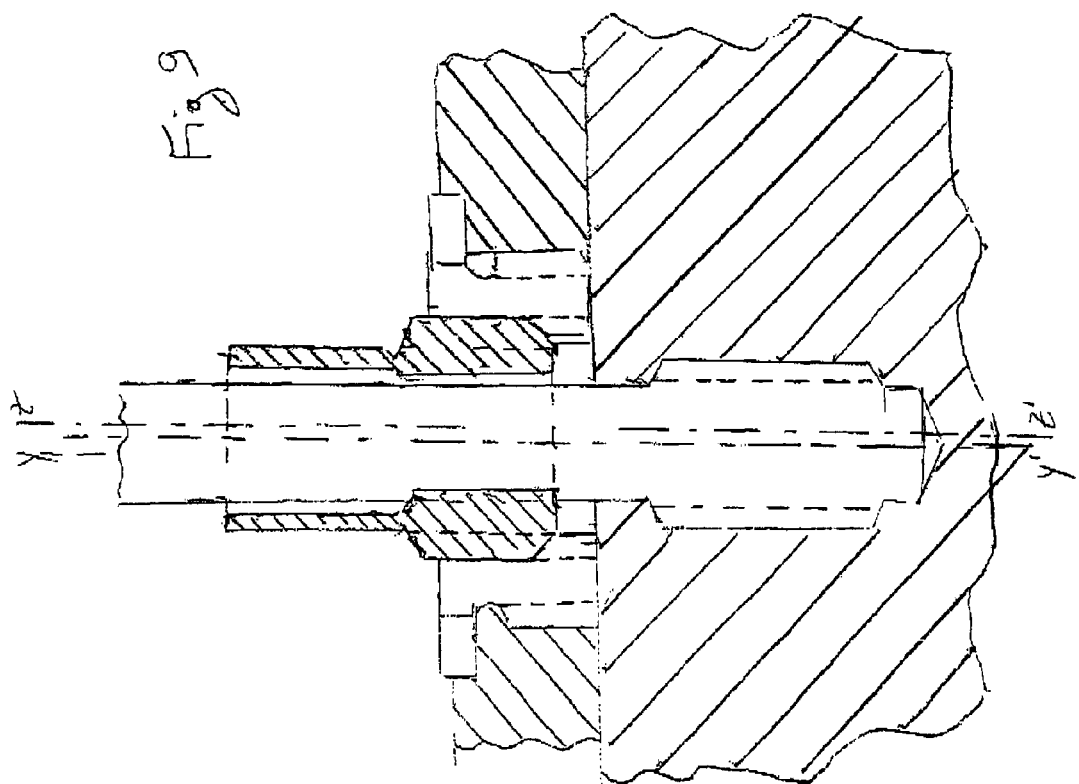

FIG. 9 is a view similar to FIGS. 1, 7 and 8, but wherein the axis of the bore of the locking sleeve is lateral in relation to the axis of the external threading of the locking sleeve. In this figure, the locking sleeve has been represented as if the pin were not present. Otherwise, it would have been difficult to show that the left part of the axial bore locks the pin.

The immobilising device shown in FIG. 1 has for its purpose to ensure connection of an osteosynthesis plate 1 on a bone part 3. To that end, the plate 1 is pierced with a threaded orifice 5 in which is screwed an intermediate sleeve 7 provided in its upper part with a flange 9 comprising notches 11 intended to ensure grip thereof in the course of its screwing in the plate 1. The flange 9 is positioned in a circular recess 10 provided in the upper part of the plate 1.

The intermediate sleeve 7 is itself pierced with a threaded central orifice 8b of which the axis zz' is inclined by an angle α with respect to the axis of revolution yy' of the intermediate sleeve 7 and of its external threading 8a.

A locking sleeve 13 is screwed by a threading 6 made in its threaded lower part 13a in the intermediate sleeve 7. The upper part 13b of this locking sleeve 13 comprises, on two of its opposite faces, flat portions 15 intended to facilitate grip of this part. The upper (13b) and lower (13a) parts of this sleeve 13 are joined by a zone of lesser resistance 17 constituted here by a circular notch.

The internal orifice 19 of the lower part 13a of the sleeve 13 of diameter d slidably receives a pin 21 provided at its lower end with a threading 23 intended to be screwed in the bone part 3. The internal bore of the upper part 13b presents a diameter D greater than that of the pin 21. Under these conditions, the immobilising device according to the invention functions as described hereinafter.

The practitioner, after having marked the position of the plate 1 that he wishes to fix on the bone part 3 and having screwed therein a boring guide (not shown in the drawing), effects a bore 24 by guiding his drill in this guide of which the longitudinal axis yy' is perpendicular to the plate.

After having replaced in the plate 1 the boring guide by the intermediate sleeve 7, the practitioner screws the lower part 21b of the threaded pin 21 in the bone part to the desired depth. He then introduces the locking sleeve 13 on the upper part 21a of the threaded rod 21 and proceeds to screw the latter in the intermediate sleeve 7, being assisted to that end by the two flat portions 15 for gripping, provided on the outer wall of the upper part 13b thereof.

It will be understood that, by reason of the angular offset α existing between the two respective axes yy' and zz', there is produced during this screwing a progressive wedging of the sleeve 13 in the intermediate sleeve 7, ending in a veritable locking creating an effect of crimping, such that, when the latter is produced, it is no longer possible thereafter to unscrew the locking sleeve 13 from the intermediate sleeve 7.

The locking in question is of the type such as that sometimes produced when a threaded element of particularly fine pitch is positioned askew in a nut, ending in a virtually undismountable connection unless the threaded element is broken. In the present case, the zone of lesser resistance, here constituted by the narrowing 17, will be determined so that, when a desired torque C is attained, rupture of the upper part 13b of the sleeve 13 is provoked.

It will then remain for the practitioner to proceed with giving the pin 21 the appropriate length, by effecting a shear thereof as close as possible to the upper part 13b of the piece 13.

An irreversible locking of the pin 21 with respect to the plate 1 is thus obtained.

The dismantling necessary for subsequent interventions is ensured by unscrewing the intermediate sleeve 7.

It will be noted that, according to the invention, unlike the plate fixing devices of the prior state of the art, this fixation of the plate on the bone part 3 is effected by exerting minimum stresses thereon, this making it possible to respect the bone parts which, most of the time, for various reasons, have lessened mechanical characteristics.

According to the invention, likewise unlike the devices of the prior state of the art, the irreversible locking created has the effect of joining in one piece the plate 1 and the threaded pin 21, which is particularly interesting insofar as, even if the mechanical resistance of the bone part lessens in the course of time, the different locking screws ensure support of the bone part. This connected structure of the bone part is all the more efficient as the plate 1 is maintained thereon by pins 21 of which the axes are not parallel.

The present invention is also interesting to reduce open fractures, i.e. to ensure the support of a plurality of bone parts without it being possible to apply to the surface of the skin a support plate.

FIG. 3 schematically shows the principle of supporting two bone part elements 3a and 3b by means of a device according to the invention. The latter is essentially constituted by a rigid support element 1a, on which are slidably mounted locking elements 30 adapted to ensure fixation of threaded pins 21 which are screwed in the bone part elements 3a and 3b.

The device for fixing the pins on the support element preferably allows a positioning of these pins in rotation so as to allow the practitioner considerable freedom of choice concerning the location of their screwing in the bone parts 3a, 3b.

Figure 4:
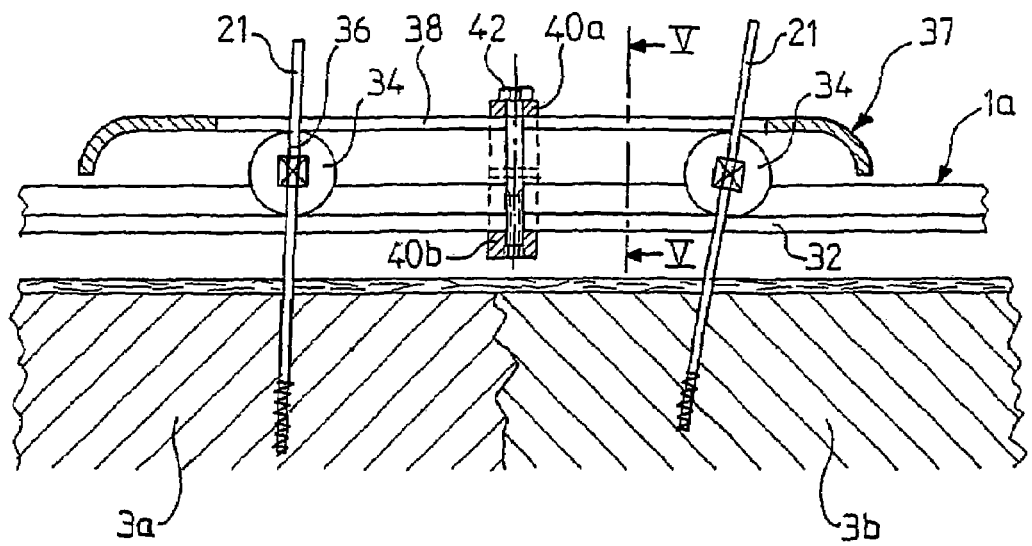
FIG. 4 is a variant embodiment of the second example of application of the present invention shown in FIG. 3.
Figure 5:
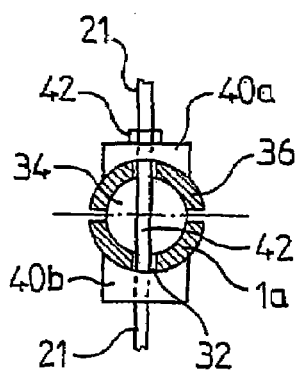
FIG. 5 is a view in partial section of the variant embodiment shown in FIG. 4 along line V-V thereof.

FIGS. 4 and 5 show a variant embodiment of a device of the type as shown in FIG. 3.

Figure 6:
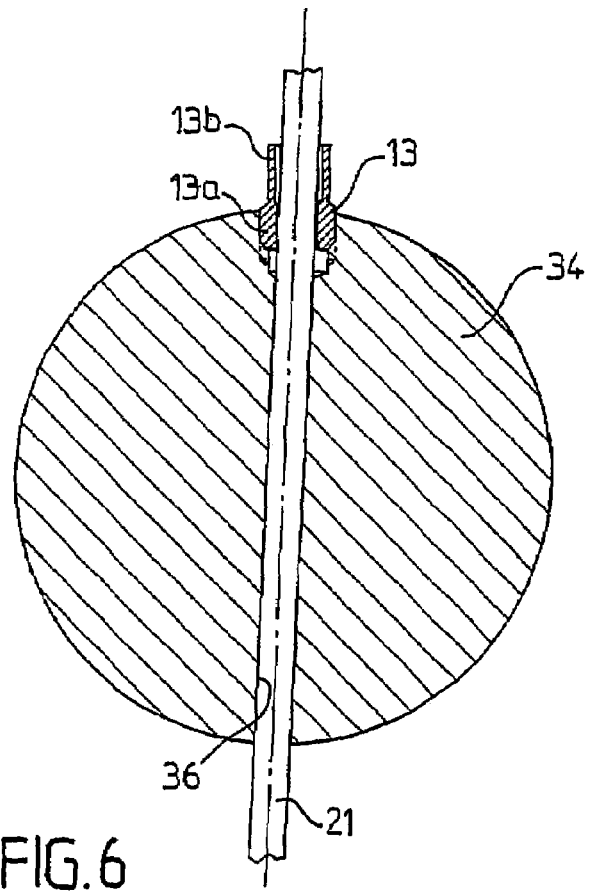
FIG. 6 is a view in section on a larger scale of a detail of embodiment shown in FIG. 4.

This device thus comprises a rail 1a constituted by a profiled metal element whose internal cross section is semi-circular in shape and whose bottom has a longitudinal slot 32 hollowed out therein, so that it constitutes a sort of chute. Inside the latter are disposed metal spheres 34 which are pierced with a diametral hole 36 allowing them to be fitted on the non-threaded part of fixing pins 21. The spheres 34 are provided with a locking/crimping device of the type such as that shown in FIGS. 1, 2 and 6, and which ensures their connection with the pins 21. This device thus allows the surgeon to position the fixing pins in the bone parts 3a and 3b in a place of his choice since he will have, on the one hand, the possibility of sliding the spheres 34 in the chute and, on the other hand, the possibility of pivoting the pin/sphere assembly through an angle of his choice.

Once the different fixing are screwed in the bone parts 3a and 3b, the irreversible connection of the spheres 34 and the respective pins 21 will be ensured as set forth in the form of embodiment described previously, then the immobilisation of each of these assemblies with respect to the support rail 1a will be ensured by covering the spheres with a longitudinal cover 37 whose internal section is semi-spherical and also provided with a longitudinal slot 38 intended to allow the pins 21 to pass, which will be strongly applied against the rail 1a by means of a stirrup element in two parts 40a, 40b which will be strongly applied against each other by a locking screw 42.

The invention claimed is:

1. Device for immobilizing with respect to a fixed element a threaded support pin screwed in a bone part along an axis, comprising a threaded locking sleeve which is connectable by screwing of the fixed element, which is provided with an axial bore which receives the pin, the axis of the threading of this sleeve is offset in relation to the axis of the pin when the pin is in place on the bone part, and/or the axis of the bore of the locking sleeve is offset in relation to the axis of the threading, wherein the fixed element is constituted by a support receiving intermediate pieces which are mounted dispacably and rotationally along a profile of the support, fixing means ensuring the immobilisation of the intermediate pieces with respect to the fixed element, and wherein said support is constituted by a rail of which an internal profile is of hemispherical shape and whose base is pierced with a longitudinal slot adapted to be traversed by the threaded pins, the intermediate pieces are constituted by spheres adapted to be positioned at any point of the rail, it comprises an upper cover of hemispherical internal profile of which the apex is pierced with a longitudinal slot adapted to be traversed by the threaded pins (21), it comprises tightening means adapted to apply the spherical intermediate pieces against the rail in order to immobilise them both in translation and in rotation with respect thereto.

* * * * *